United States Patent
Wilson et al.

[11] Patent Number: 6,149,629
[45] Date of Patent: Nov. 21, 2000

[54] MEDICAL NEEDLE SAFETY APPARATUS AND METHODS

[75] Inventors: Michael A. Wilson, Salem; Gale H. Thorne, Bountiful, both of Utah

[73] Assignee: Specialized Health Products, Inc., Bountiful, Utah

[21] Appl. No.: 09/312,317

[22] Filed: May 14, 1999

[51] Int. Cl.$^7$ ............................................... A61M 5/32
[52] U.S. Cl. ........................ 604/198; 604/187; 604/192
[58] Field of Search .................. 604/181, 187, 604/192, 198, 27, 506, 171, 264, 268, 272

[56] References Cited

U.S. PATENT DOCUMENTS

| | | | |
|---|---|---|---|
| Re. 34,045 | 8/1992 | McFarland | 604/198 |
| 4,573,976 | 3/1986 | Sampson et al. | 604/198 |
| 4,772,272 | 9/1988 | McFarland | 604/198 |
| 5,026,356 | 6/1991 | Smith | 604/192 |
| 5,219,333 | 6/1993 | Sagstetter et al. | 604/110 |
| 5,356,392 | 10/1994 | Firth et al. | 604/198 |
| 5,411,492 | 5/1995 | Sturman et al. | 604/263 |
| 5,466,223 | 11/1995 | Bressler | 604/192 |
| 5,879,331 | 3/1999 | Osterlind | 604/110 |

*Primary Examiner*—Wynn Wood Coggins
*Assistant Examiner*—Catherine Serke
*Attorney, Agent, or Firm*—Gale H. Thorne; Paul S. Evans

[57] ABSTRACT

An invention which provides for making low cost apparatus and one-hand activation methods for shielding a syringe needle as a safety precaution after each needle use. A shield, which may be used as a protective cover for the needle during initial transport to site of use, is linearly actuated to three distinct stops by action of a single hand, thereby leaving the second hand of a user free for patient care. The shield is releasable from two of the three stops to make possible uncovering of the needle preparatory to use and temporary needle protection between needle uses. The shield has an elongated hollow barrel shape which is sized to fit snugly about, yet slide smoothly over a body of a syringe associated with the needle. The barrel shape of the shield is longitudinally interrupted by a scissure in which an arm which is hingeably affixed to the shield resides. The arm is selectively bent to provide operative surfaces which permit the shield to be released from two of the three stops and further displaced to selected stops by inward depression of the arm. The invention utilizes a collet with a slot and a pawl which interacts with at least one set of ratchet teeth on the arm to provide one of the releasable stops. Generally release from stops is actuated by inward pressure on a predetermined portion of the arm.

8 Claims, 6 Drawing Sheets

MEDICAL NEEDLE SAFETY APPARATUS AND METHODS

FIELD OF INVENTION

This invention relates generally to safety devices for hollow bore medical needles and particularly to syringe needle devices which are used with a syringe barrel and which comprise protective needle sheaths for securely shielding sharp medical needle tips, both before and after being used in a medical procedure. This invention more particularly relates to sheaths or shrouds which may be used to protect a sharpened needle tip in transit before use, ad interim after a preliminary use, such as filling a syringe with a medication, and extended to a locked, needle-covering position after a medical procedure is completed.

PRIOR ART

Problems associated with inadvertent needle sticks are well known in the art of blood sampling, percutaneous medication injection and other medical procedures involving uses of medical needles. Ever increasing attention is being paid to needle stick problems due to the contemporary sensitivity of exposure to AIDS, Hepatitis and other serious blood-borne diseases.

Commonly, procedures involving removing a needle from a patient require a technician to use one hand to place pressure at the wound site where the needle is being withdrawn while removing the needle apparatus with the other hand. It is common practice for a tending technician to give higher priority to care for the wound than is given to disposal of a needle. In the case of commonly used, non-safety devices such priority either requires convenience of an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to take appropriate procedures to properly dispose of a used, exposed needle while caring for a patient. Further, common practice of filling syringes with medication in one area and then transporting an uncapped needle (recapping a needle is currently discouraged in U.S. medical practice due to dangers associated with recapping) to a patient area provides a significant opportunity for accidental needle sticks.

Widespread knowledge and history associated with needle care and disposal problems have resulted in conception and disclosure of a large number of devices each of which represents an attempt to provide not only a solution to the problem of needle sticks, but also a device which is commercially viable (i.e. cost and price competitive with currently used non-safety devices). In the case of syringes, current devices which are used to shield syringe needles often require two hands and safety status of needle shields are not readily apparent.

Examples of disclosures of safety devices which protect needles by moving a protective shield over a sharp end of a syringe or other hollow bore medical needle are found in U.S. Pat. No. 5,348,544, issued Sep. 20, 1994 to Sweeney et al. (Sweeney), U.S. Pat. No. 5,246,428 issued Sep. 21, 1993 to Donald W. Falknor (Falknor), U.S. Pat. No. 5,256,153 issued Oct. 26, 1993 to Lawrence W. Hake (Hake) and U.S. Pat. Nos. 5,139,489 and 5,154,285, issued Aug. 18, 1992 and Oct. 13, 1992, respectively, to William H. Hollister (Hollister). There are many other examples of safety devices which retract needles into housings, however, this instant invention is more directly related to devices which extend a shield over a needle rather than to those which employ needle retraction.

Sweeney discloses a device comprising a guard which is manually, slidably movable along a needle cannula from a site proximal to a user to a distal site where the needle tip is shielded. The device comprises a hinged arm which extends along the needle cannula and which is moved distally to collapse upon itself to extend the shield over the tip. Access to the tip is denied by a metallic clip. An alternative embodiment is also disclosed by which the manual operation is augmented by a spring. A device based upon Sweeney is currently being distributed by Becton Dickinson and Company, Franklin Lakes, N.J. in which three separate parts (two injection molded and one metal clip) are used to mechanize the guard. Once the device is extended to shield a needle tip, it cannot be easily reset to recover use of the needle for a subsequent procedure. Also, the hinged arm requires activation in the region of the needle itself and comprises parts which are of a size which occasionally impedes a user's line of sight to insertion locations. The device based upon Sweeney is not readily resettable from a safety condition to a reuse state.

Falkner, and related disclosures, disclose devices comprising shields which are automatically releasible to extend distally from a user to cover a needle. The devices comprise latch mechanisms which are manually switched between unlatched and latched positions to free the needle for use and lock the shield over the needle, respectively. Of course, position of the latch mechanism provides a visual interpretation of the safety of the device (i.e. whether or not a latch is engaged), but that is the only safety mechanism and a "missed" indicator of latch mechanism position may be possible in stressful circumstances. When the latch mechanism is in the unlatched position, access to the needle is not only possible, but likely when the front of the device is impacted by a body part. In addition, the shield, though made of transparent material, covers a portion of an attached syringe body until fully extended and may make reading portions of volume measurement indicia on the syringe body difficult to read with accuracy when the syringe is being used in a titrating application.

Hake is representative of disclosure of devices comprising a manually slidable guard which is disposed over a syringe body during a medical procedure involving a medical syringe needle and manually, slidably moved distally into a needle guarding position usually at the end of the procedure. Commonly users of such devices complain of difficulty of seeing measurement indicia while the guard is disposed over the syringe body and of danger of inadvertent needle sticks while sliding the guard distally to cover the needle. As well, it is generally difficult to determine whether a guard is in a locked or unlocked state when it covers the needle, making an additional possibility of inadvertent needle sticks.

Hollister discloses a needle protection device which may be used with a double-ended needle assembly or with a simpler single needle system. The protection device comprises a substantially rigid housing flexibly connected to a container (for a vacuum tube sampling system) or to a needle hub. To exercise the protection device, the rigid member is pivotally rotated into engagement with an exposed needle of the double-ended needle assembly and is securely affixed to the exposed needle. A major drawback of the needle protection device of Hollister is the size and position of the rigid housing. During use of an assembly or system in a medical procedure, length and position of the housing member is considered by some to be inconvenient. A second drawback is the requirement either for two handed operation to pivot the housing to engage the needle or for the requirement to find and use a stable support surface against which the housing is pressed while the needle is swung into engagement with the housing. In a currently marketed format, an integral container holder version of the device disclosed by Hollister comprises two injection molded parts which permit the housing to be rotated, as much as possible, out of the way during a medical procedure. Such a format requires five injection molded parts, including a disposable needle assembly.

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary items currently on the market, those devices are usually not found to be commercially viable.

BRIEF SUMMARY AND OBJECTS OF THE INVENTION

In brief summary, the novel invention disclosed herein dramatically diminishes known major problems resulting from injury-related needle sticks which occur when needle tips are bared as medical needles are withdrawn from a patient at the end of a needle insertion procedure, but, perhaps more important to general patient welfare, these inventions provide opportunity for fabrication of a very low cost safety needle system which may result in wider acceptance and greater likelihood of broader use. Low cost is achieved by a dramatic reduction in injection molded parts wherein a needle covering safety sheath also serves as a needle cap, a part which is commonly provided for all known contemporary syringe needles and integral syringe/ syringe needle devices.

This novel invention provides apparatus by which a syringe needle affixed to a barrel is selectively covered and temporarily shielded by a safety shield during transport and otherwise prior to use in a medical application, unshielded for use and, then, either temporarily shielded awaiting future use or permanently shielded when the needle is no longer to be used. Generally, a device based upon the invention provides a slidable shield which comprises a hollow cylindrical sheath having a distal end which is closed but for a small aperture through which a syringe needle extends for use in a medical procedure. The hollow cylinder is sized to fit snugly but slidably about an associated syringe barrel and has a scissure which provides a track whereby the hollow cylinder is linearly constrained when displaced proximally and distally. The cylinder is constrained to slide proximally and distally along the syringe barrel by the natural enclosing curvature of the cylinder about the barrel and by an arm which distends proximally from the end through a slotted part affixed to the barrel.

The arm, slotted part and sheath, in combination, have three linearly aligned stops disposed along the length, thereof. Selective operation of the arm causes a controlled release at two of the three stops. No such release is so achievable at the third stop. The slotted part has a pawl which interacts with the arm and, at least one set of ratchet teeth disposed on the arm to provide at least one releasible detent position along the length of the arm. Optionally, the sheath comprises one or more medially oriented catches disposed along the scissure which interact with the slotted part in a latch/catch manner to provide one or more of the stops. The arm has a series of bends which provide release points which when depressed by pressure from a digit of a hand selectively forces release of the pawl and ratchet teeth at positions having a ratchet stop. Similarly, a similar depression of the arm is used to release a latch from a catch where a latch/catch stop is present at a release position. In this manner, the cylinder is displaced to any of the three positions and displaced from the two release positions by action of a single hand.

The first, releasible, position is an intermediate placement where the cylinder acts as a displaceable protective cover for use while transporting a syringe needle affixed to the syringe barrel. The second, releasible position is at a displacement whereat the cylinder is proximally disposed to bare the syringe needle and its sharpened tip for use. The third position is at a site where the cylinder is securely and permanently affixed to protectively cover the needle tip.

Release from the first and second positions is accomplished by a pressure applied against the arm to force the arm toward the syringe barrel and to, thereby, disengage either ratchet teeth stop of the arm from the pawl of the slotted part or a latch from a catch. Bends upon the arm also provide outwardly distending curvatures which provide opportunity for applying appropriately directed, either proximal or distal, force to facilitate direction of desired movement when displacing the cylinder from the first position to the second position and vice versa and when displacing the cylinder from the first to the third position.

Accordingly, it is a primary object to provide a manually actuated safety sheath for a medical needle which consists of a single injection molded cylinder shield part and another single injection molded slotted part.

It is a particularly important object to provide a safety sheath which acts as a protective cover for a syringe needle and its sharpened tip in a first displacement, which acts as a temporary safety shield in a second displacement and which acts as a permanent safety shield in a third displacement.

It is a another important object to provide a sheath having three linear displacements which are stable, with positive action being required by a user to displace the sheath from two of the sites to another selected site.

It is a very important object to provide a safety sheath having a plurality of linearly disposed displacement positions each having a different safety state, the status of the sheath at each site being readily visually verifiable.

It is also an important object to provide a shroud which averts contact with the needle along the length of the needle when the shroud is displaced to protect the needle and its tip.

These and other objects and features of the present invention will be apparent from the detailed description taken with reference to accompanying drawings.

DETAILED DESCRIPTION OF THE ILLUSTRATED EMBODIMENTS

In this description, unless a specific object is referenced, the term proximal is used to indicate the segment of a device normally closest to a user (the clinician or technician who is treating a patient). In like manner, the term distal refers to the other (away from the user) end. Reference is now made to the embodiments illustrated in FIGS. 1–6 wherein like numerals are used to designate like parts throughout.

Figure 1:
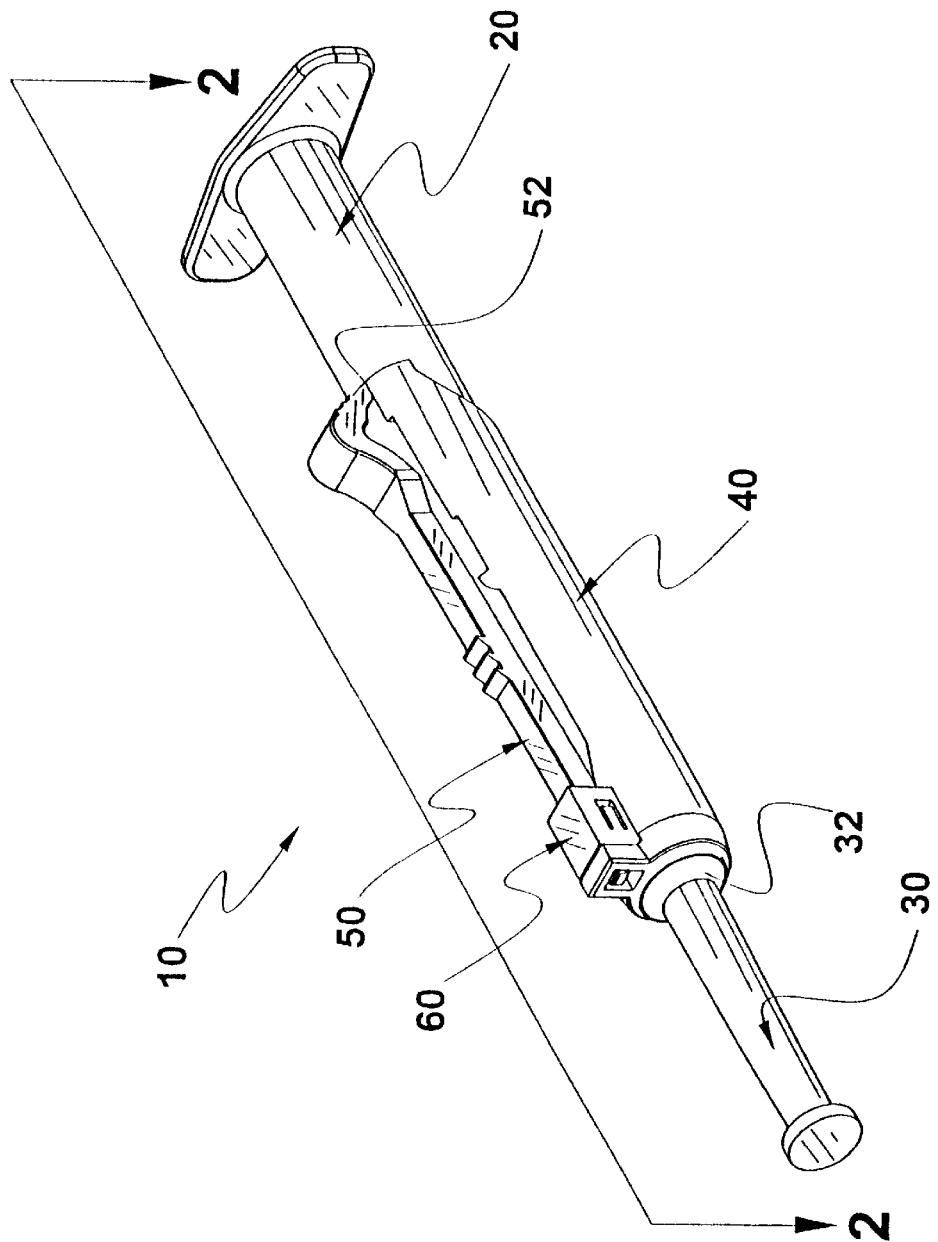
FIG. 1 is a perspective of a device based upon the instant invention, the device including a syringe barrel part having a proximally disposed slidable shield and a distally disposed needle cover affixed thereto.

As may be observed in FIG. 1, a device 10 which is in accord with the instant invention is seen in association with a syringe barrel 20 and a needle cover 30. Such barrels 20 and needle cover 30 are well known in the medical art. Note that needle cover 30 is disposed through a distally disposed orifice 32, of device 10, to obtain connective access to a needle hub. Device 10 comprises an elongated shield 40, an elongated arm 50 preferably affixed thereto by a hinge 52 and a slotted part 60. As is apparent from one displacement of shield 40, as disclosed hereafter, cover 30 may be supplanted by sleeve 40 disposed to provide temporary needle protection during shipment and storage.

Figure 2:
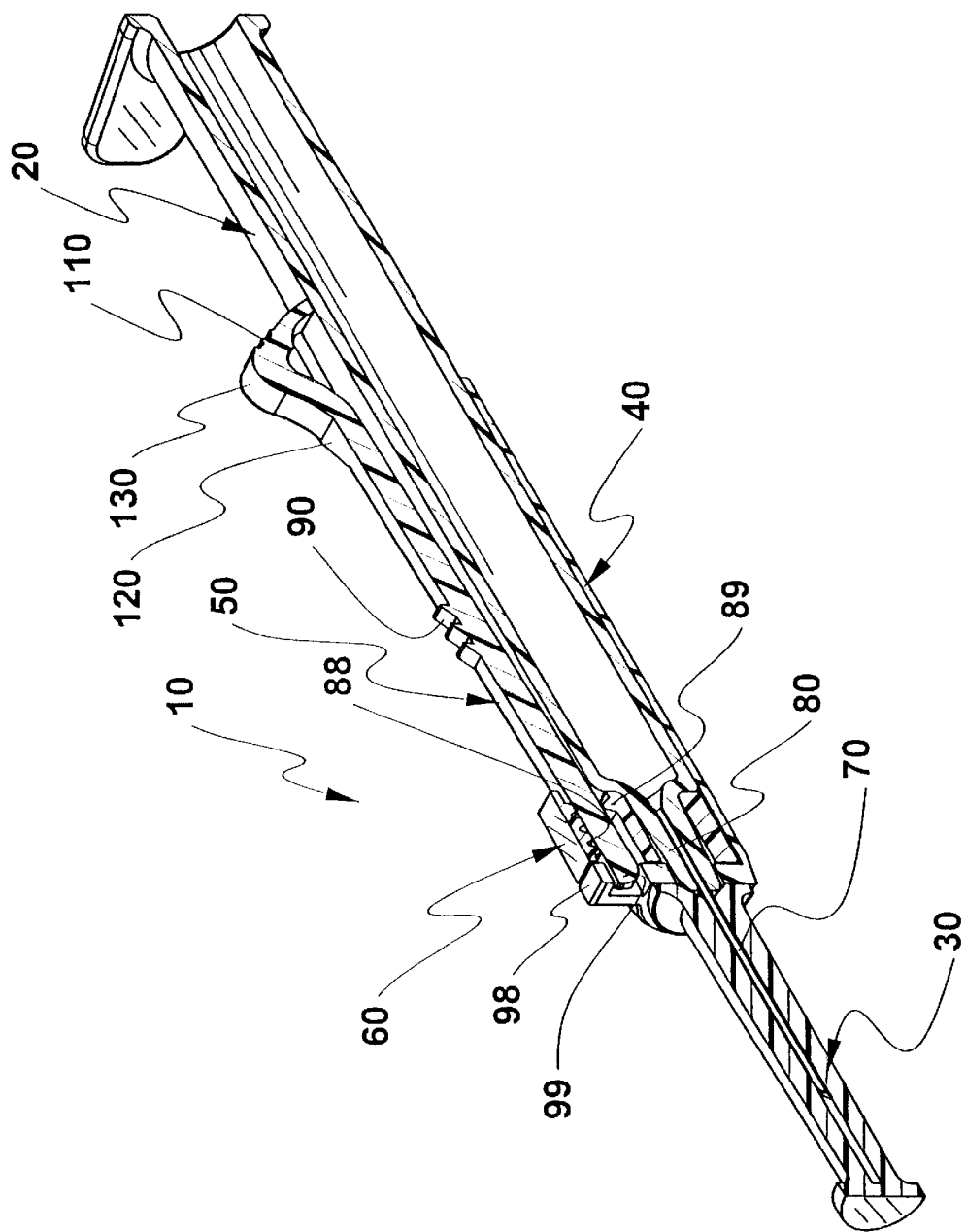
FIG. 2 is a cross section taken along lines 2—2 of FIG. 1 wherein an integral needle is seen.
Figure 3:
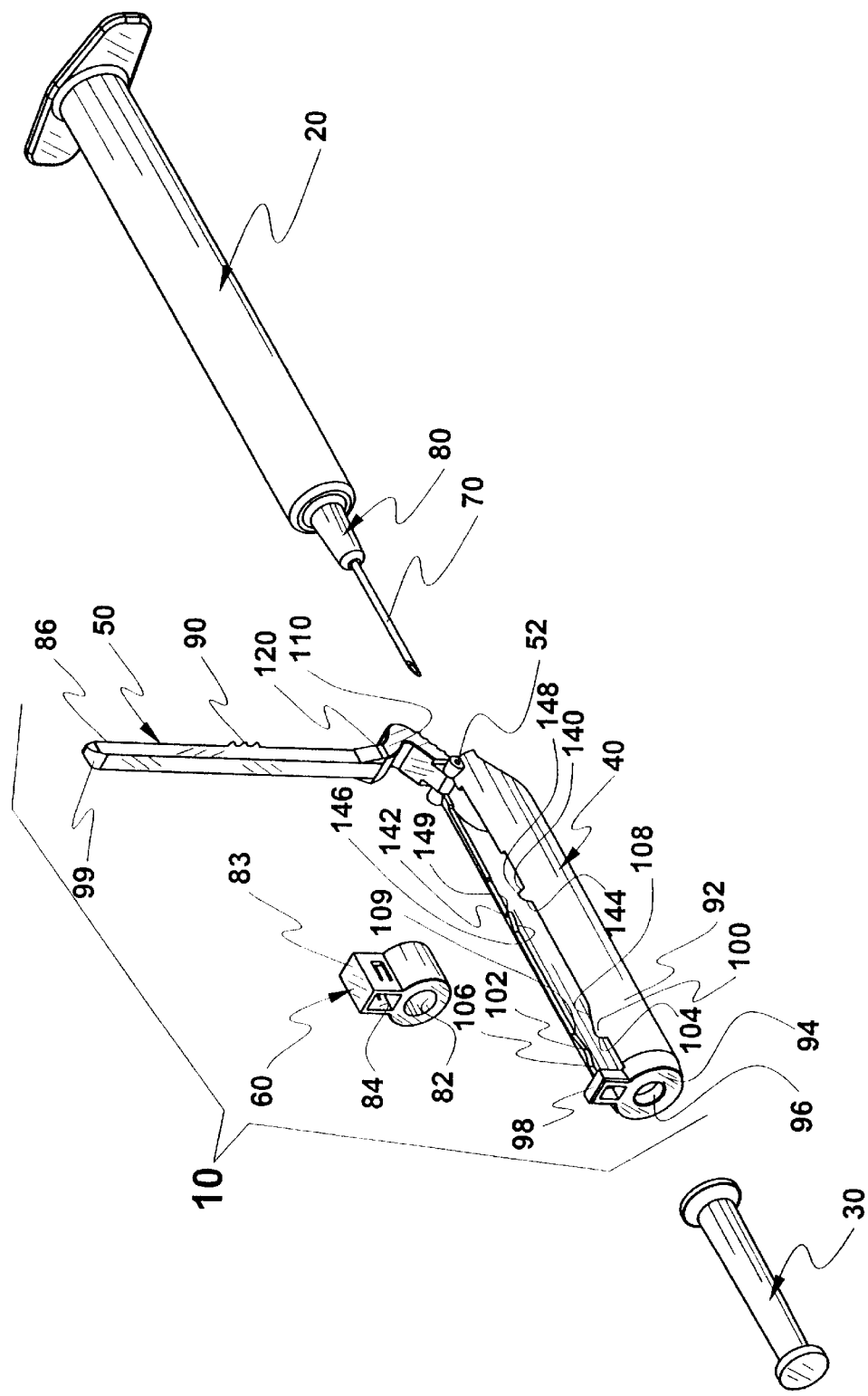
FIG. 3 is an exploded perspective of the parts which are seen in FIG. 1.

Parts of device 10 and other parts associated with device 10 are seen in more detail in FIGS. 2 and 3. As is standard for integrally affixed syringe barrels and syringe needles, a syringe needle 70 is securely affixed to barrel 20 via a needle hub, which in the case of an integrally affixed needle 70 is also a distally disposed luer fitting 80, as seen in FIGS. 2 and 3. In this embodiment, slotted part 60 is affixed, preferably by adhesion, to luer fitting 80.

However, the paramount issue is that the shield be constrained in stable displacement relative to syringe needle 70. For this reason and to reduce manufacturing cost, slotted part 60 may be molded as an integral part of syringe barrel 20 which is securely affixed during use to a needle, usually through a luer fitting. Also, as it is common for a syringe needle to be affixed to a syringe barrel by a luer fitting to make the syringe needle separable from the barrel, it is appropriate, in such circumstances, to mold slotted part 60 as a part of the needle hub.

To provide a needle shield which provides a safety shield for a combination of contemporary standard (non-safety) syringe barrel and standard (non-safety) syringe needle, slotted part 60 may be provided as part of a separate apparatus having a luer fitting for proximal attachment to the syringe barrel (preferably a luer lock fitting) and a complementary distal luer fitting whereby slotted part 60 is affixed to the syringe needle.

As seen in FIG. 3, slotted part 60 comprises an orifice 82 whereby slotted part 60 is affixed to barrel 20 at luer fitting 80. Note that orifice 82 is generally concentric with a communicating fluid passageway between syringe barrel 20 and needle 70. Slotted part 60 further has protruding section 83 which further comprises a second orifice 84 which is sized and configured to permit a distal portion 86 of arm 50 to pass therethrough. As is better seen in FIG. 2, slotted part 60 comprises an inwardly disposed undulating pattern 88 and a compressible biasing member 89 which act as a pawl for ratchet teeth superiorly disposed upon arm 50. While slotted part may be made from a synthetic resinous material such as polypropylene, it is preferably made from a more resilient material, such as nylon, although slotted part 60 may be made from the material from which barrel 20 is made when slotted part 60 is integrally molded therewith.

Arm 50 comprises a set of superiorly disposed ratchet teeth 90 as seen in FIGS. 2 and 3. While only one set of ratchet teeth 90 is disposed upon arm 50, other ratchet teeth may be disposed along arm 50 within the scope of the instant invention. Note, that if ratchet teeth are disposed on arm 50 to communicate with undulating pattern 88 when arm 50 is disposed as seen in FIGS. 1 and 2, arm 50 must be designed to releasibly disengage those ratchet teeth from undulating pattern 88 such that arm 50 can be selectively moved distally.

Shield 40 comprises an elongated, slotted hollow cylindrical part 92 proximally disposed relative to a more distal blunted end segment 94. End segment 94 comprises an orifice 96 through which needle 70 passes as shield 40 is displaced between shielding and non-shielding positions. End segment 94 also comprises a clasp 98 for holding arm 50, especially a distal portion 99 of arm 50, in place such that arm 50 is held in linear alignment with orifice 84. Note that arm 50 is hingedly affixed to shield 40 through a hing 52. Hinge 52 is preferably a living hinge, permitting shield 40 and arm 50 to be molded as a single injection molded part. Shield 40 and arm 50 are preferably molded as a single integral molded part.

As best seen in FIG. 3, shield 40 comprises a juxtaposed first pair of stops 100 and 102 which act upon protruding section 83 to selectively restrain shield 40 in a needle 70 baring proximal disposition. Stops 100 and 102 each comprise protruding section 83 movement impeding, distal convex surfaces 104 and 106. Arm 50 is fabricated to be at a non-parallel, upwardly disposed acute angle relative to barrel 20. Pressing arm 50, at a first pressure point 110, toward syringe barrel 20 laterally displaces stops 100 and 102 to permit shield 40 to be longitudinally, distally displaced. Such displacement moves shield 40 to protectively cover needle 70. Displacement of shield 40 until ratchet teeth 90 are engaged with the pawl of undulating pattern 88, provides a temporary safety shield about needle 70. Such a displacement is seen in FIG. 4.

Figure 4:
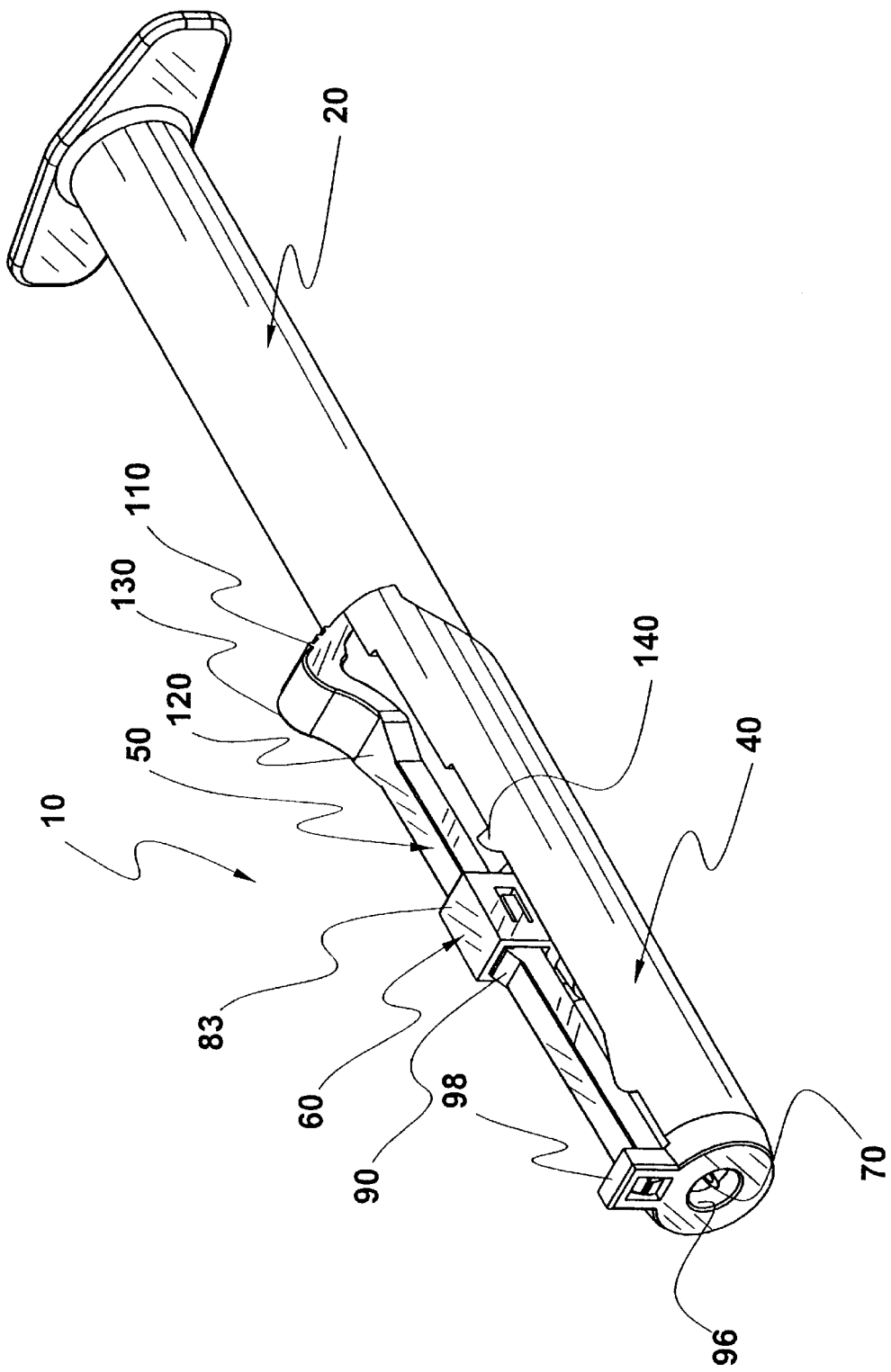
FIG. 4 is a perspective of the device of FIG. 1 with the needle cover removed and the slidable shield disposed to cover the otherwise exposed needle.
Figure 5:
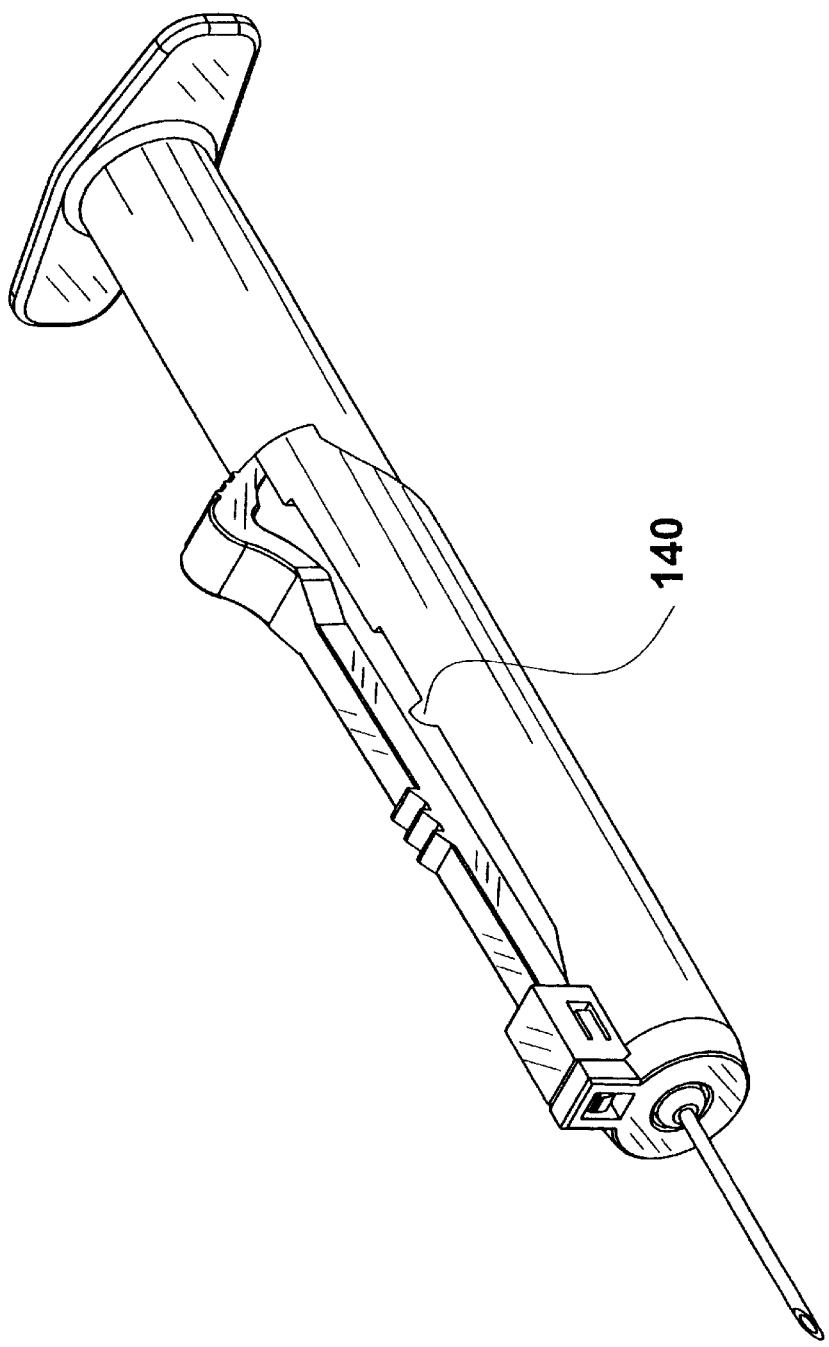
FIG. 5 is a perspective of the device of FIG. 1 with the needle cover removed and the slidable shield proximally disposed to expose the needle for use.

Noting in FIG. 4, with arm 50 disposed at the site of the temporary safety shield, a further depression of arm 50 at a second pressure point 120 releases ratchet teeth 90 from undulating pattern 88 and permits shield 40 to be proximally displaced. A convex bend 130 in arm 50 provides a convenient place where a thumb or forefinger acts upon arm 50 when releasing and simultaneously so displacing arm 50 and, therefore, shield 40. In this manner, shield 40 is displaced from being a temporary safety shield to a site where needle 70 is bared for use, as seen in FIG. 5. Note, as best seen in FIG. 3, that stops 100 and 102 each comprise a slightly impeding, but not severely restricting, proximally disposed surfaces, 108 and 109.

Figure 6:
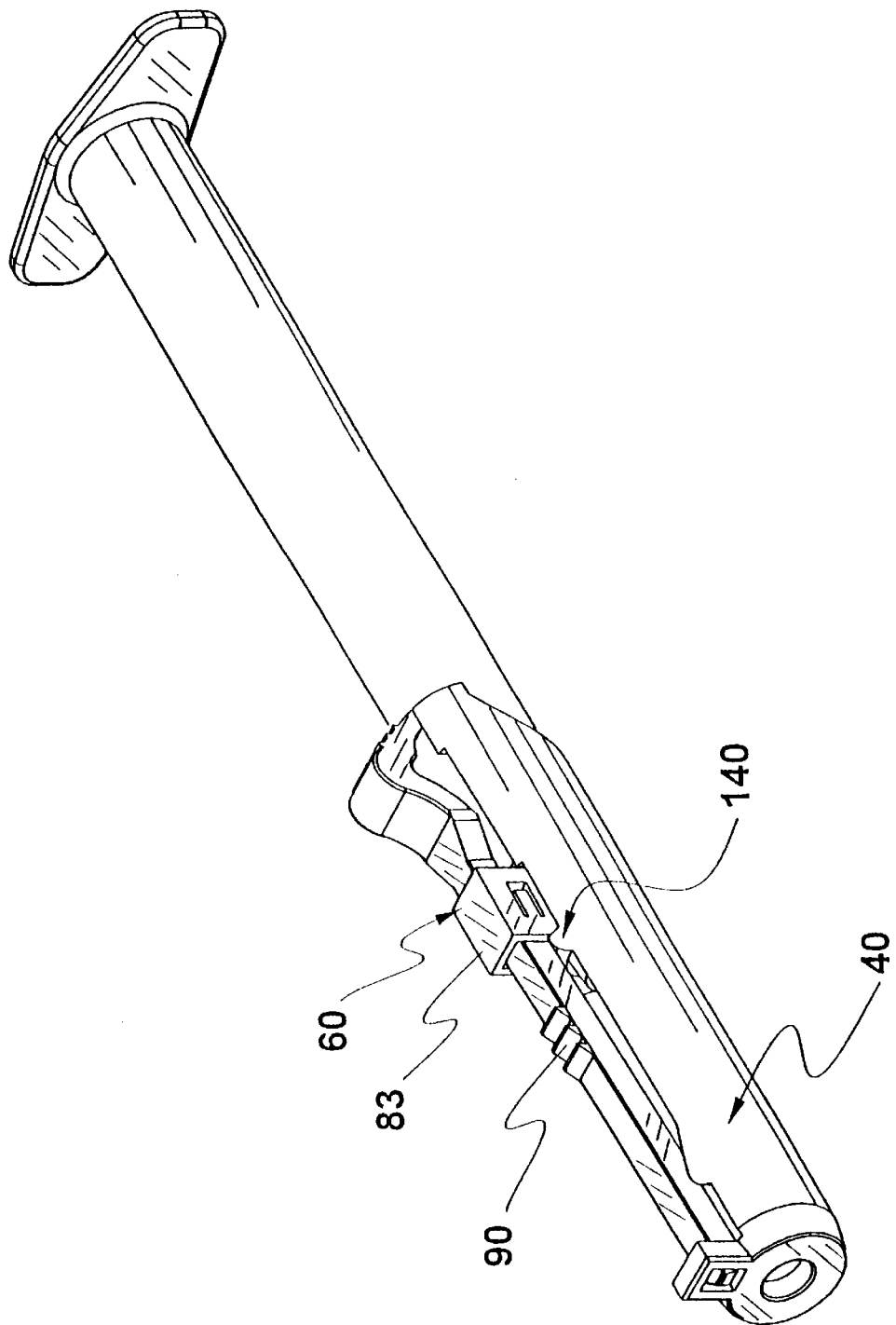
FIG. 6 is a perspective of the device of FIG. 1 with the needle cover removed and the slidable shield disposed to cover the needle in an irreversibly affixed displacement.

As may be noted in FIGS. 3–6, shield 40 comprises a second pair of juxtaposed stops, 140 and 142 (see FIG. 3). Stops 140 and 142 comprise rounded distal surfaces 144 and 146 and abruptly blunted proximal surfaces 148 and 149. Stops 140 and 142 are so shaped to permit facile distal displacement of shield 40 distally, but securely retain protruding section 83 and guard against proximal displacement of shield 40 once it has been forced thereby. Displacement of shield 40 to a permanently locked in place state is seen in FIG. 6.

The invention disclosed herein may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety shield apparatus having a displaceable needle shield which is at least partially disposed about a needle connecting device associated with a medical syringe needle and which is linearly displaced to predetermined positions such that the medical syringe needle may be selectively uncovered for use and recovered for safety a number of times during a medical procedure, said apparatus comprising:

the needle connecting device comprising a needle hub to which the syringe needle is securely affixed;

a slotted part securely affixed relative to said needle hub, said slotted part comprising an outwardly protruding section which further comprises a linearly accessible orifice which is sized and configured to permit a distal portion of an elongated arm to pass therethrough, the outwardly protruding section being further sized and configured to be constrained to linear displacement along a track formed by a scissure in the needle shield and comprising an inwardly disposed undulating pattern with a ratchet interface and a releasable biasing member which forces engagement of the ratchet interface unless acted upon by forces, communicated through the arm, which cause the ratchet interface to be offset, disengaged and thereby released;

the needle shield comprising an elongated hollow cylindrical part having the scissure disposed along the long axis of the cylindrical part to thereby provide the track for the outwardly protruding section of the slotted part whereby the hollow cylindrical part is constrained to linear displacement when said needle shield is displaced proximally and distally, said needle shield further comprising an abrupt, open distal end wherethrough the medical needle is selectively displaceable, without contacting said hollow cylindrical part;

said hollow cylindrical part further comprising an end segment comprising a clasp, aligned with the scissure, for holding a distal end of the elongated arm in place such that the elongated arm is in linear alignment with said open distal end;

the elongated arm being affixed at a proximal end thereof to a proximal end of said hollow cylindrical part such that said arm is disposed in alignment with the scissure, the clasp and the slotted part, said elongated arm comprising at least one set of ratchet teeth which in combination with said undulating pattern and biasing member form the ratchet interface, said arm further comprising at least one bend which provides a first pressure point, pressure upon which causes an offset which disengages the ratchet interface to permit selective proximal displacement of the needle shield and a second pressure point which, when acted upon, distally displaces the needle shield to cover the syringe needle for safety;

in combination, said slotted part and said cylindrical part about said scissure comprising a releasible first stop for said needle shield whereat the needle is bared for use; and said ratchet interface in combination with said releasible biasing member comprising a second stop for said needle shield whereat the needle is enclosed within a selectively displaceable safety barrier.

2. The safety shield apparatus according to claim 1 wherein said slotted part and said cylindrical part about said scissure, in combination, comprise a third stop linearly aligned with said first and second stops, said third stop being proximally disposed in said scissure relative to said first and second stops whereat an unreleasible lock, whereby the shield is securely affixed as a safety cover for the syringe needle at the third stop, is provided.

3. The safety shield apparatus according to claim 2 wherein said shield comprises at least one catch medially disposed in said scissure at a predetermined site against which the slotted part acts as a locking latch to form the third stop.

4. The safety shield apparatus according to claim 1 wherein, in combination, said arm and said cylindrical part comprise a hinge connection whereby the elongated arm is affixed to the proximal end of the hollow cylindrical part.

5. The safety shield apparatus according to claim 1 wherein said shield comprises at least one catch disposed in said scissure at a predetermined site against which the slotted part acts as a latch to form the first stop.

6. A method for displacing a safety needle shield to protect a medical syringe needle when a medical syringe needle is used a plurality of times, comprising the steps of:

(a) providing a safety shield apparatus comprising:

a displaceable needle shield which is at least partially disposed about a needle connecting device associated with a medical syringe needle and which is linearly displaced to predetermined positions such that the medical syringe needle may be selectively uncovered for use and recovered for safety a number of times during a medical procedure;

the needle connecting device comprising a needle hub to which the syringe needle is securely affixed;

a slotted part securely affixed relative to said needle hub, said slotted part comprising an outwardly protruding section which further comprises a linearly accessible orifice which is sized and configured to permit a distal portion of an elongated arm to pass therethrough, the outwardly protruding section being further sized and configured to be constrained to linear displacement along a track formed by a scissure in the needle shield and comprising an inwardly disposed undulating pattern with a ratchet interface and a releasable biasing member which forces engagement of the ratchet interface unless acted upon by forces, communicated through the arm, which cause the ratchet interface to be offset, disengaged and thereby released;

the needle shield comprising an elongated hollow cylindrical part having the scissure disposed along the long axis of the cylindrical part to thereby provide the track for the outwardly protruding section of the slotted part whereby the hollow cylindrical part is constrained to linear displacement when said needle shield is displaced proximally and distally, said needle shield further comprising an abrupt, open distal end wherethrough the medical needle is selectively displaceable, without contacting said hollow cylindrical part;

said hollow cylindrical part further comprising an end segment comprising a clasp, aligned with the scissure, for holding a distal end of the elongated arm in place such that the elongated arm is in linear alignment with said open distal end;

the elongated arm being affixed at a proximal end thereof to a proximal end of said hollow cylindrical part such that said arm is disposed in alignment with the scissure, the clasp and the slotted part, said elongated arm comprising at least one set of ratchet teeth which in combination with said undulating pattern and biasing member form the ratchet interface, said arm further comprising at least one bend which provides a first pressure point, pressure upon which causes an offset which disengages the ratchet interface to permit selective proximal displacement of the needle shield and a second pressure point which, when acted upon, distally displaces the needle shield to cover the syringe needle for safety;

in combination, said slotted part as a latch and said cylindrical part about said scissure as a first catch comprising a releasible first stop for said needle shield whereat the needle is bared for use; and said ratchet interface in combination with said releasible biasing member comprising a second stop for said needle shield whereat the needle is enclosed within a selectively displaceable safety barrier;

(b) displacing the shield distally to the second stop to protectively enclose the needle;

(c) preparatory for use, applying pressure to the first pressure point on the elongated arm to release the shield at the second stop and to linearly displace the shield to the first stop where the needle is bared for use;

(d) after use, applying pressure to the second pressure point to release the shield from the first stop and linearly displacing the shield to the second stop whereat the needle is again protectively enclosed and the shield is securely but releasibly affixed thereat; and (e) repeating steps (c) and (d) until a medical procedure associated with use of the safety shield apparatus is complete.

7. The method according to claim 6 comprising the further steps of:

(f) providing a combination whereby said slotted part and said cylindrical part about said scissure, comprise a third stop linearly aligned with said first and second stops, said third stop being proximally disposed in said scissure relative to said first and second stops to provide a lock whereby the shield is securely and unreleasibly affixed as a safety cover for the syringe needle at the third stop; and (g) after final use, applying pressure to the arm to release the shield from the first catch at the second stop and to linearly displace the shield to the third stop to unreleasibly lock the needle shield in a safety configuration over the syringe needle.

8. A safety shield apparatus having a displaceable needle shield which is at least partially disposed about a needle connecting device associated with a medical syringe needle and which is linearly displaced to predetermined needle shielding positions such that the medical syringe needle may be selectively uncovered for use and recovered for safety a number of times during a medical procedure, said apparatus comprising:

the needle connecting device comprising a needle hub to which the syringe needle is securely affixed;

a slotted part securely affixed relative to said needle hub, said slotted part comprising an outwardly protruding section which further comprises a linearly accessible orifice which is sized and configured to permit a distal portion of an elongated arm to pass therethrough, the outwardly protruding section being further sized and configured to be constrained to linear displacement along a track formed by a scissure in the needle shield and comprising an inwardly disposed undulating pattern with a ratchet interface and a releasable biasing member which forces engagement of the ratchet interface unless acted upon by forces, communicated through the arm, which cause the ratchet interface to be offset, disengaged and thereby released;

the needle shield comprising an elongated hollow cylindrical part having the scissure disposed along the long axis of the cylindrical part to thereby provide the track for the outwardly protruding section of the slotted part whereby the hollow cylindrical part is constrained to linear displacement when said needle shield is displaced proximally and distally, said needle shield further comprising an abrupt, open distal end wherethrough the medical needle is selectively displaceable, without contacting said hollow cylindrical part;

said hollow cylindrical part further comprising an end segment comprising a clasp, aligned with the scissure, for holding a distal end of the elongated arm in place such that the elongated arm is in linear alignment with said open distal end;

the elongated arm being affixed at a proximal end thereof to a proximal end of said hollow cylindrical part such that said arm is disposed in alignment with the scissure, the clasp and the slotted part, said elongated arm comprising at least one set of ratchet teeth which in combination with said undulating pattern and biasing member form the ratchet interface, said arm further comprising at least one bend which provides a first pressure point, pressure upon which causes an offset which disengages the ratchet interface to permit selective proximal displacement of the needle shield and a second pressure point which, when acted upon, distally displaces the needle shield to cover the syringe needle for safety;

in combination, said slotted part and said cylindrical part about said scissure comprising a releasible first stop for said needle shield whereat the needle is bared for use; and said ratchet interface in combination with said releasible biasing member comprising a second stop for said needle shield whereat the needle is enclosed within a selectively displaceable safety barrier; and said slotted part and said cylindrical part about said scissure, in combination, comprising a third stop linearly aligned with said first and second stops, said third stop being proximally disposed in said scissure relative to said first and second stops to provide an unreleasible lock, whereby the shield is securely affixed as a safety cover for the syringe needle at the third stop.

* * * * *